United States Patent [19]

Khonsari et al.

[11] Patent Number: 4,851,086
[45] Date of Patent: Jul. 25, 1989

[54] PRODUCTION OF HIGH PURITY PHENOL BY STEAM DISTILLATION

[75] Inventors: Ali M. Khonsari, Bloomfield; Jamin Chen, Montville; George D. Suciu, Ridgewood, all of N.J.; William B. Fisher; Lamberto Crescentini, both of Chester, Va.

[73] Assignees: The Lummus Company, Bloomfield; Allied Corporation, Morris Township, Morris County, both of N.J. ; part interest to each

[21] Appl. No.: 547,403

[22] Filed: Oct. 31, 1983

[51] Int. Cl.⁴ .................. B01D 3/38; C07C 37/76
[52] U.S. Cl. .................................. 203/38; 203/39; 203/45; 203/83; 203/85; 203/96; 568/754
[58] Field of Search .............. 203/38, 92, 93, 95–98, 203/39, 43–46, 52, 53, 59, 69, 83, 85; 568/754

[56] References Cited

U.S. PATENT DOCUMENTS

| | | | |
|---|---|---|---|
| 2,344,791 | 3/1944 | Stoesser | 203/97 |
| 2,862,855 | 12/1958 | Lang et al. | 203/97 |
| 2,971,893 | 2/1961 | Hood | 203/87 |
| 3,029,293 | 4/1962 | Nixon | 568/754 |
| 3,298,933 | 1/1967 | Prahl et al. | 203/39 |
| 3,335,070 | 8/1967 | Adams | 203/83 |
| 4,298,765 | 11/1981 | Cochran et al. | 568/754 |
| 4,351,967 | 9/1982 | Nishimura et al. | 568/754 |
| 4,532,012 | 7/1985 | Khonsari et al. | 203/53 |

Primary Examiner—Wilbur Bascomb
Attorney, Agent, or Firm—Elliot M. Olstein

[57] ABSTRACT

Crude phenol, containing AMS by-product, and MBF impurity, is distilled in the presence of water to separate MBF impurity.

11 Claims, 1 Drawing Sheet

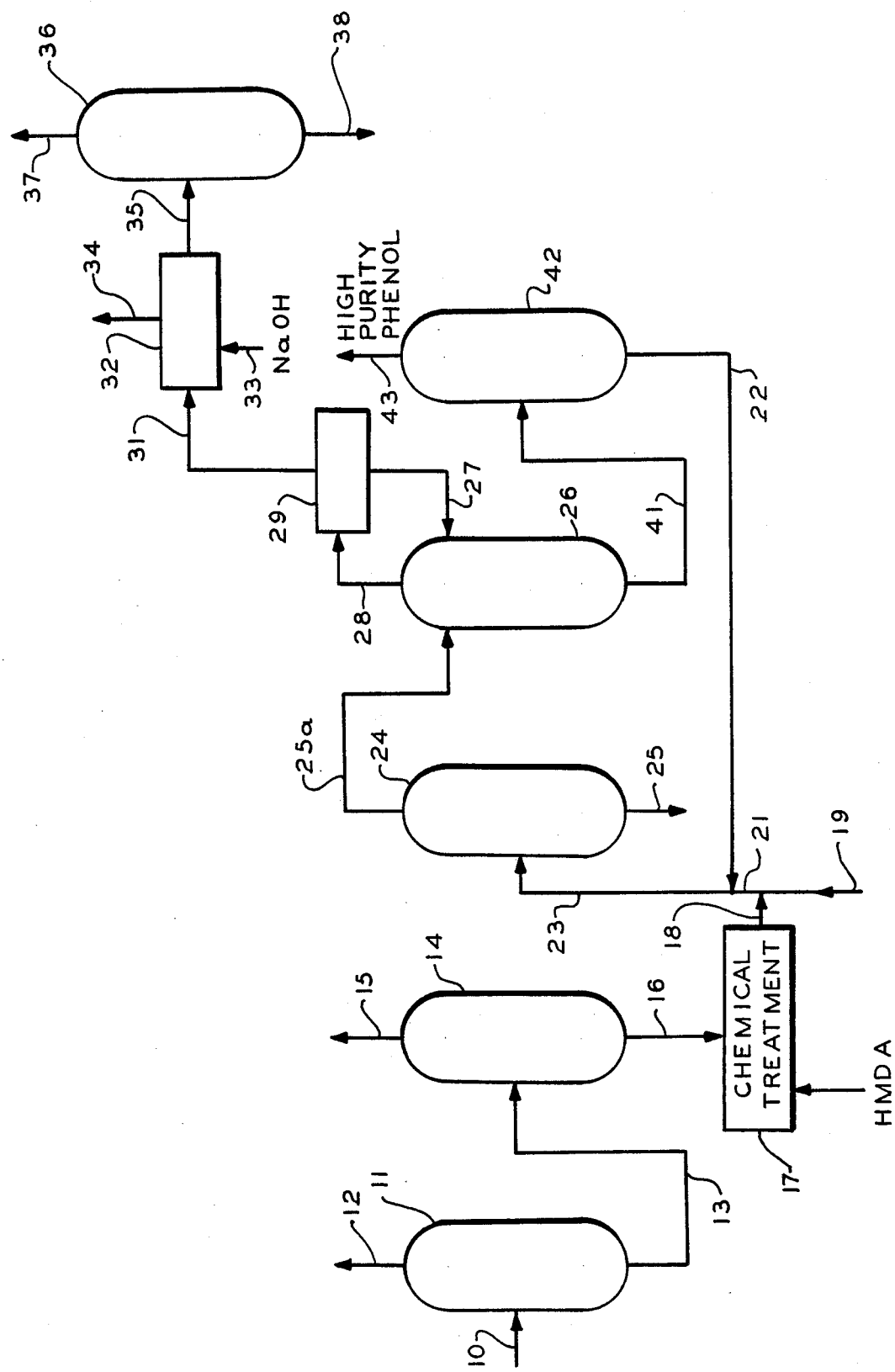

PRODUCTION OF HIGH PURITY PHENOL BY STEAM DISTILLATION

This invention relates to the production of phenol, and more particularly, to the production of high purity phenol.

Phenol may be produced from cumene by the oxidation of cumene to cumene hydroperoxide, followed by cleavage of the hydroperoxide to phenol and acetone.

In such a process, the reaction product is introduced into a separation and recovery system wherein the crude product is initially treated in a distillation column to separate acetone byproduct from the remaining mixture. The acetone-free product is then introduced into a further distillation column which operates to separate cumene from the remaining product. Optionally, the cumene recovery column can be operated to recover alpha-methylstyrene (AMS) with the cumene. If the AMS is not recovered with the cumene, the product remaining from the cumene column is introduced into a crude AMS column to separate AMS from the remaining mixture.

The product remaining from the cumene recovery column, or the crude AMS column (in the case where AMS is recovered separately from the cumene), is then introduced into a phenol recovery column to separate phenol from remaining higher boiling components.

The thus recovered crude phenol includes impurities such as acetol, mesityl oxide (MO), acetophenone, 2- and 3-methyl-benzofurans (collectively or individually methylbenzofuran or MBF), etc.

In one process, the crude phenol is chemically treated to reduce the amount of acetol and MO present in the crude phenol. Thus, for example, the crude phenol may be treated with an amine, followed by the addition of acid or acid anhydride, as disclosed, for example, in U.S. Pat. No. 3,692,845.

The resulting product is referred to as a resin or "one" grade phenol.

U.S. Pat. No. 4,298,765 describes a procedure for recovering a high purity phenol wherein, after treatment with amine, and optionally an acid or acid anhydride, the treated phenol is distilled in the presence of water to recover from the top of the column a phenol-water azeotrope which contains the majority of the MBF and other impurities initially present in the treated phenol. Water present in the azeotrope is treated to separate MBF and other impurities so as to enable recycle of such water to the distillation.

In accordance with U.S. Pat. No. 4,298,765, the water in the overhead is treated, after an initial separation from, a phenol phase, with a solvent to extract organics therefrom, or the phenol-water mixture is treated with a solvent, followed by phase separation of organics. In such a process, a significant portion of the phenol present in the overhead is recovered in the organic phase, and it is then necessary to separately treat such organic phase to recover such significant portion of phenol. Such recovery increases overall costs.

In accordance with one aspect of the present invention, there is provided an improvement in a process for producing phenol by oxidation of cumene to cumene hydroperoxide, and cleavage of cumene hydroperoxide to phenol and acetone wherein a phenol product recovered from the process includes AMS produced as by-product in the process, and optionally some cumene, which further includes MBF impurity, and is distilled in the presence of water to recover a heavy product of phenol having a reduced quantity of MBF and a light product containing water, AMS, cumene (if cumene is present in the phenol feed to the distilling) and phenol.

Thus, in accordance with the present invention, AMS, generated as by-product in the production of phenol, is maintained in the phenol product introduced into the distillation column wherein the phenol is distilled in the presence of water to separate MBF in a light product and provide a heavier phenol product having a reduced quantity of MBF.

More particularly, in accordance with one aspect of the present invention, there is provided an improvement in a process for producing phenol by oxidation of cumene to cumene hydroperoxide, followed by cleavage of cumene hydroperoxide to phenol and acetone wherein crude phenol, containing AMS and optionally some cumene, as well as impurities comprising MBF, mesityl oxide, acetol and higher boiling impurities, is treated with an amine to reduce the quantity of acetol and mesityl oxide. Subsequent to the amine treatment, phenol which still contains AMS(and some cumene if the cumene was present in the crude phenol) and impurities comprising MBF, is subjected to distillation in the presence of water to recover a heavy product comprising phenol containing a reduced amount of MBF and a light product, containing water, AMS, any cumene added to the column and phenol. Prior to the distillation in the presence of water (either before or after, preferably after, treatment with the amine), high boiling components are separated from the phenol by a coarse distillation.

The AMS maintained in the phenol introduced into the column can function as an extraction solvent in the condensed overhead recovered from the column. More particularly, condensation of the overhead from the azeotropic distillation column produces a water phase and an organic phase, with the MBF present in the overhead being extracted into the AMS of the organic phase, thereby permitting recycle of all or a portion of the water phase (the water phase includes some phenol) to the azeotropic distillation column.

In addition, the presence of AMS (and generally also some cumene) in the azeotropic distillation column permits a reduction in the amount of water required in the column, which reduces the amount of phenol recovered in the light product. Thus, the presence of the AMS in the column permits a reduction in the ratio of water to phenol used in the column, as compared to such distillation in the absence of extraction solvent in the column.

As a result of maintaining AMS by-product in the phenol product introduced into the distillation column, it is possible to separate MBF in the overhead fraction by use of a weight ratio of weight to phenol which is as low as 0.05:1, preferably at least 0.1:1. In general, such a result can be accomplished with a water to phenol ratio which does not exceed 0.8:1, and most generally does not exceed 0.5:1.

The amount (weight) of AMS and cumene or AMS alone (solvent) required in order to perform the separation of the MBF with reduced water is a multiple of the amount (weight) of the MBF present. For the range of MBF concentrations usually present in the crude phenol (30–200 ppm), the solvent is generally employed in an amount of at least 0.5%, with the solvent amount generally not exceeding 10% and most generally not exceeding 7%, all by weight, based on phenol.

The amount of solvent employed should be minimized consistent with effective removal of impurities in the light product in that an increase in the amount of solvent will necessitate an increase in the amount of water in the column, which results in a corresponding increase in the amount of phenol in the light product.

Thus, in accordance with the preferred embodiment, the amount of AMS and cumene retained in the phenol is the amount minimally required for removal of impurities in the light product, and the water is employed in the amount minimally required for removing the solvent in the light product to thereby minimize the amount of phenol in the light product.

The overhead fraction recovered from the distillation has a reduced amount of phenol, and such overhead is separated into an organic phase comprising the solvent, impurities and some phenol, and a water phase comprising some phenol and water, which water phase may be recycled to the distillation.

As hereinbefore indicated, the AMS by-product and optionally also some cumene is maintained in the phenol product fed to the distillation. More particularly, the phenol fed to the distillation is initially derived from the cumene recovery column which is in the separation and recovery section of the phenol production plant, and the subsequent chemical treatment of such crude phenol to reduce the content of acetol and MO is effected in a manner such that the AMS(and generally some cumene) which is present in the crude phenol subjected to such chemical treatment remains in the chemically treated phenol. In accordance with prior art procedures, if cumene and/or AMS were present in the crude phenol subjected to chemical treatment, such AMS and/or cumene were removed (distilled) as lighter products during the chemical treatment. For example, the AMS and/or cumene may be retained in the chemically treated phenol by operating under reflux conditions.

In accordance with a preferred procedure, after the chemical treatment (or prior thereto), the phenol is introduced into a coarse distillation column to remove higher boilers (those present in the phenol from the cumene recovery column and/or those formed in the chemical treatment) prior to the distillation in the presence of water.

The use of a combination of water and AMS and optionally also cumene (solvent) in the distillation column, as hereinabove noted, reduces the amount of phenol recovered in the light (overhead) product, which reduces the overall cost of the purification.

The water and solvent, as well as the water and phenol, are recovered as azeotropes in the overhead product, along with the impurities. It has been found that a heavy product (bottoms) of phenol can be recovered which is essentially free of solvent and water and which contains MBF in an amount no greater than 10–25 ppm, as compared to an MBF content in the feed in the order of 50–200 ppm.

It is to be understood that it is not necessary to remove all of the solvent as overhead (some solvent can be recovered in the phenol bottoms in that the solvent may be subsequently separated from the phenol. It is preferred, however, to minimize (and most preferably eliminate) the solvent from the phenol bottoms.

Although it is preferred to operate at the lower water to phenol ratios hereinabove described, it is also possible to operate at higher ratios, in which case, the AMS and optionally cumene, still functions as an extraction solvent in the condensed overhead.

The overhead product from the distillation column is condensed, and the condensed product is separated into an organic and an aqueous phase. The separated aqueous phase may be recycled to the distillation. Appropriate amounts of makeup water are added to the recycle in order to compensate for the water which may have dissolved in the organic phase. The makeup water need not be pure. Any aqueous stream from the phenol plant can be used if it is similar in composition with the recycled stream.

Although recycling of the entire water phase to the distillation is preferred, it is to be understood that all or a portion of the water phase may not be recycled to the column, but treated in a known manner for recovering phenol values therefrom (for example, by distillation, etc.)

The separated organic phase, which contains the solvent (AMS alone or AMS and cumene), MBF and other impurities, and some phenol, after separation from the aqueous phase, may then be treated in any of the known ways, such as with a base (for example, sodium hydroxide) to recover any phenol present therein in an aqueous phase in which the phenol dissovles as a phenate. Such water soluble phenate may be subjected to a "springing" operation, as known in the art, in order to recover the phenol.

The distillation of crude phenol is generally accomplished in a distillation column, which when operated at approxiamtely atmospheric pressure, will have an overhead temperature of from 98° C. to 99° C., and a bottoms temperature from 182° C. to 185° C.. The operating pressure can be atmospheric, or either higher or lower than atmospheric pressure, without departing from the teachings of the invention (the overhead temperature is the boiling temperature of the azeotrope at the prevailing pressure). It should be understood that the overhead and bottoms temperatures will vary with the pressure employed, moisture and amount of solvents used.

The composition of the product recovered at the top of the tower corresponds, or is close to that of mixtures of the azeotropes formed from the phenol, solvent and water at the operating pressure.

The phenol recovered as a bottoms product from the distillation procedure, in the presence of water, includes heavier components, and such phenol bottoms product may then be further treated to separate phenol from the heavier components; for example, the phenol bottoms may then be treated by a further distillation to separate high purity phenol from such heavier components.

The crude phenol feed employed in the distillation in the presence of water and solvent, as hereinabove noted, is one which has been chemically treated in order to reduce the content of acetol and MO. As hereinabove noted, such treatment may be accomplished by use of a base, and in particular, an amine, and optionally an acid or acid anhydride to neutralize the amine. It should be understood, however, that the present invention is not limited to such a feed.

The invention will be further described with reference to the drawing, wherein:

The drawing is a simplified schematic flow diagram of a preferred embodiment of the present invention.

It is to be understood, however, that the scope of the invention is not limited to the preferred embodiment.

Referring now to the drawing, a reaction effluent recovered from the reaction section of a procedure for producing phenol by the oxidation of cumene to cumene hydroperoxide, followed by acid cleavage of the hydroperoxide to phenol and acetone, in line 10, includes, as principal components, phenol, acetone, cumene, alphamethylstyrene, and as primary impurities, MBF, acetophenone, acetol, MO, etc., is introduced into an acetone recovery column, schematically designated as 11, which is operated so as to recover acetone as an overhead through line 12, and a remaining bottoms product through line 13.

The bottoms product in line 13 is introduced into a cumene recovery column, generally designated as 14, operated at conditions to recover cumene and AMS as overhead through line 15. The cumene recovery column 14 is specifically operated in a manner such that there is AMS present in the bottoms product recovered through line 16 for use, as hereinafter described, in the procedure of the present invention directed to separation of MBF from phenol. In general, there is also some cumene in the bottoms product.

The bottoms in line 16 includes phenol, as well as cumene and AMS, and as impurities, MO, MBF, acetol and acetophenone, etc.

The bottoms in line 16 is then introduced into a chemical treatment zone, schematically generally indicated as 17, wherein the bottoms is treated with an amine to reduce the quantity of acetol and MO in the crude phenol. The amine is preferably hexamethylenediamine. The chemical treatment is effected in a manner such that acetol and MO are converted to higher boiling components. In accordance with the present process, chemical treatment is accomplished in a manner such that the cumene and AMS remain in the liquid phase, as compared to the prior art procedure wherein cumene and AMS concentrate in the vapor phase and are removed from the crude phenol product.

The chemically treated phenol from chemical treatment zone 17, in line 18, is then optionally treated with acid provided through line 19 (in particular phthalic anhydride), so as to neutralize the base used in the chemical treatment. The acid treated stream in line 21 is combined with heavier components, in line 22, obtained as hereinafter described, and the combined stream in line 23 is introduced into a column, schematically generally indicated as 24, in which a coarse distillation operation is performed, in order to separate higher boiling components, from the crude phenol stream introduced through line 23. As hereinabove indicated, the acid addition may be eliminated without adversely affecting the process.

The heavier components recovered from column 24 through line 25 may then be further treated by procedures known in the art, in order to recover more of the phenol contained therein.

The overhead stream recovered from column 24 through line 25a includes phenol, as well as cumene and AMS, which will function as the organic solvent in the subsequent distillation, and as impurities, MBF, small amounts of MO, some acetone and other impurities. The crude phenol in line 25a is essentially free of materials which boil higher than acetophenone. The crude phenol in line 25a is introduced into the upper portion of an azeotropic distillation column, schematically generally indicated as 26, along with an aqueous phase, in line 27, obtained as hereinafter described.

The column 26 is provided with a suitable known means for effecting heating thereof, such as a side boiler (not shown). Alternatively, live steam may be introduced into the azeotropic column 26.

The column is operated at a temperature and pressure to separate impurities from phenol, e.g., the conditions hereinabove described. Azeotropes, which include water, phenol, the cumene-AMS solvent and impurities, such as MBF and the like, are recovered from the top of the column through line 28.

The overhead in line 28 is cooled (not shown) in order to effect condensation thereof. The condensed overhead is introduced into a separation zone, schematically generally indicated as 29 to separate the condensed overhead into an aqueous phase and an organic phase.

The aqueous phase, which is comprised of phenol and water, and which contains a reduced amount of impurities, is recycled to the column 26 through line 27.

The separated organic phase, comprised of the AMS and cumene, which function as an extraction solvent, as well as phenol, and impurities, including MBF, is withdrawn from the separation zone 29 through line 31 and introduced into zone 32, wherein the organic phase is contacted with aqueous base, such as sodium hydroxide, introduced through line 33 for the purpose of converting any phenol to sodium phenate, which is water soluble, while MBF and other impurities are not, whereby they remain in the organic solvent. Such recovery of phenol from an organic phase is well known in the art, and no further details are required for a complete understanding of the present invention.

Aqueous sodium phenate is recovered from zone 32 through line 34 for subsequent treatment to recover phenol.

The organic phase, which is now essentially free of phenol, is withdrawn from zone 32 through line 35 for further treatment, as required, in order to recover cumene therefrom, for recycle, as feed to the phenol production. For example, as shown in the drawing, the organics in line 35 are introduced into a distillation column 36 operated to recover cumene as overhead through line 37, and AMS and heavier components, including MBF and other impurities, as a bottoms, through line 38. The bottoms in line 38 may be further treated, as desired.

The phenol, recovered from the azeotropic distillation column 26 through line 41, is introduced into a phenol recovery column, schematically generally indicated as 42 in order to separate phenol from higher boiling impurities. A high purity phenol is recovered from column 42 through line 43.

The heavier components recovered as bottoms from column 42 in line 22 are ultimately recovered from the system with the bottoms recovered from column 24.

The high purity phenol recovered from column 42 in line 43 contains less than 30 ppm of MBF, and in most cases less than 10 ppm of MBF.

Although the invention has been described with respect to a preferred embodiment in the accompanying drawing, it is to be understood that the scope of the invention is not limited to such an embodiment.

Thus, for example, the embodiment may be modified in numerous ways within the spirit and scope of the present invention. In one such modification, crude phenol recovered from the cumene column 14 may be initially treated to separate heavier components therefrom, followed by the chemical treatment to reduce the quantity of acetol and MO.

In another modification, the crude phenol may be chemically treated in the cumene recovery column.

These and other modifications should be apparent to those skilled in the art from the teachings herein.

The invention will be described with respect to the following example; however, the scope of the invention is not limited thereby:

EXAMPLE

Product from the bottom of the cumene recovery column (column 14 of the drawing) was treated with HMDA and PAA in order to remove the ketonic impurities. The heavy boilers present in the original phenol or formed during the chemical treatment were separated by a coarse distillation of the chemically treated product (column 24 of the drawing).

The overhead product from the coarse distillation was submitted to azeotropic distillation with water.

A continuously operated Oldershaw column with 1" ID, provided with 52 actual trays, was used.

Phenol and water were metered, mixed, preheated to 90° C. and fed on the 50th tray of the column (counting from the bottom).

Phenol depleted of MBF and other impurities is withdrawn continuously from the reboiler of the column. The vapors which leave the 52nd (top) tray of the column are condensed. The liquid overhead product separates into an aqueous phase and an organic phase.

The feed and products corresponding to a period of 5 hours of continuous operation were collected and analyzed.

During the run 780 g of phenol and 380 g $H_2O$ were fed ($H_2O$/Phenol=0.49). The overhead product consisted of 53 g organic phase and 400 g aqueous phase. The purified phenol was recovered as 676 g bottom product.

The composition of the various streams is reported in the table.

| Sample Description | Acetone | MO | Cumene | AMS | MBF | AP | DMPC | Phenol |
|---|---|---|---|---|---|---|---|---|
| Phenol feed | 131 | 14 | 582 | 33530 | 112 | 2700 | 97 | Balance |
| Bottom Prod. | 1 | — | — | 36 | 19 | 2429 | 95 | Balance |
| Ovhd Org Phase | 1016 | 202 | 8656 | 47.64* | 1575 | 5021 | 160 | 36.52* |
| Ovhd Aq. Phase | 205 | — | 3 | 255 | — | 21 | — | 4.87* |

*Concentrations in wt %, all other figures are concentrations in ppm.
AP = acetophenone
DMPC = Dimethyl phenyl carbinol The present invention is particularly advantageous in that AMS by-product produced in the process is effectively utilized in the recovery of high purity phenol.

In addtion, by proceeding in accordance with the present invention, it is possible to eliminate the phenol column normally used in the phenol production plant.

Furthermore, the use of AMS in the azeotrope column results in improved recovery of phenol by permitting a reduction in the amount of water used in the column.

These and other advantages should be apparent to those skilled in the art from the teachings herein.

Numerous modifications and variations of the present invention are possible in light of the above teachings and, therefore, within the scope of the appended claims, the invention may be practiced otherwise than as particularly described.

What is claimed is:

1. In a process for producing high purity phenol wherein alpha-methylstyrene is produced as a by-product, the improvement comprising:
   recovering a phenol product which includes alphamethylstyrene produced as by-product and further includes methylbenzofuran impurity; retaining alpha-methylstyrene produced as by-product in the phenol product, said recovering and retaining of alpha-methylstyrene produced as by-product being in an amount of at least 0.5%, by weight, based on phenol subjected to steam distilling; steam distilling said phenol product containing said retained alpha-methylstyrene produced as by-product in an amount of at least 0.5%, and no greater than 10%, by weight, based on phenol, with a water to phenol ratio of at least 0.05:1 and no greater than 0.8:1 to recover a light product comprising phenol, water, alphamethylstyrene and methyl-benzofuran and a heavy product comprised of phenol having a reduced quantity of methyl-benzofurans; and distilling the heavy product to recover high purity phenol.

2. The process of claim 1 wherein the phenol product further includes cumene.

3. The process of claim 1 wherein the water to phenol ratio does not exceed 0.5:1.

4. The process of claim 3 wherein the retained (AMS) alpha-methylstyrene does not exceed 7% of the phenol subjected to the distilling.

5. The process of claim 3 wherein the heavy product contains no greater than 10 to 25 ppm of (MBF) methylbenzofuran.

6. In a process for producing phenol by oxidation of cumene to cumene hydroperoxide and cleavage of cumene hydroperoxide to phenol and acetone wherein alpha-methylstyrene is produced as by-product, the improvement comprising:
   recovering a phenol product which includes methylbenzofuran impurity and a member selected from the group consisting of (a) alpha-methylstyrene produced as by-product and (b) alphamethylstyrene produced as by-product and some unreacted cumene, said product being essentially free of materials which are higher boiling than acetophenone; retaining said member in said phenol product, said recovering and retaining of said member being in an amount to provide at least 0.5% by weight, of the member based on phenol subjected to steam distilling; steam distilling said phenol product in the presence of water to provide steam and said retained member, said water being present in an amount to provide a water to phenol ratio of at least 0.05 to 1 and no greater than 0.8 to 1, said retained member being present in an amount to provide at least 0.5%, by weight, of the member based on phenol and a phenol bottom product from the steam distilling containing no greater than 10 to 25 ppm of methylbenzofuran and which is free of said member and water, said steam distilling being operated at an overhead temperature corresponding to an azeotropic boiling temperature of overhead product; recovering said phenol bottom product, recovering an overhead product comprising said member, methyl-benzofuran, water and some phenol; and distilling the phenol bottom product to recover high purity phenol.

7. The process of claim 6 wherein the water to phenol ratio is no greater than 0.5:1.

8. The process of claim 6 wherein said member is retained in an amount no greater than 7%, by weight, based on phenol.

9. In a process for producing phenol by oxidation of cumene to cumene hydroperoxide, followed by cleavage of cumene hydroperoxide to phenol and acetone, wherein alpha-methylstyrene is produced as by-product, the improvement comprising:

recovering a crude phenol product comprising phenol, some unreacted cumene, alpha-methylstyrene produced as by-product and impurities comprising methyl-benzofuran, mesityl oxide, acetol, and higher boiling impurities; treating the crude phenol with an amine to reduce the quantity of acetol and mesityl oxide and recover a treated phenol comprising phenol, cumene, alpha-methylstyrene produced as by-product, higher boiling components and impurities comprising methylbenzofuran; initially distilling the treated phenol to separate higher boiling components and produce a phenol overhead comprising phenol, alpha-methylstyrene produced as by-product, cumene and impurities comprising methyl-benzofuran, said recovering, treating and initially distilling being effected to retain alpha-methylstyrene produced as by-product in said phenol overhead in an amount of at least 0.5%, by weight, based on phenol subjected to steam distilling; subsequently steam distilling the phenol overhead containing retained alphamethylstyrene produced as by-product in an amount of at least 0.5% by weight based on phenol, with a water to phenol ratio of at least 0.05:1 and no greater than 0.8:1 to recover a phenol bottoms product containing a reduced amount of methyl-benzofuran and an overhead product comprising water, alpha-methylstyrene, cumene, phenol and methyl-benzofuran impurities; condensing the overhead product to produce an organic phase comprising alpha-methylstyrene, cumene, some phenol and extracted methyl-benzofuran and an aqueous phase comprising water and phenol suitable for recycle to the subsequent distilling; and distilling the phenol bottoms product to recover high purity phenol.

10. The process of claim 9 wherein water to phenol ratio does not exceed 0.5:1.

11. The process of claim 10 wherein the bottoms product contains no greater than 10 to 25 ppm of methyl-benzofuran (MBF).

* * * * *